(12) United States Patent
Johnson et al.

(10) Patent No.: US 6,911,040 B2
(45) Date of Patent: Jun. 28, 2005

(54) COVERED SEGMENTED STENT

(75) Inventors: Kirk Johnson, Weston, FL (US); Pedro L. Diaz, Pines, FL (US)

(73) Assignee: Cordis Corporation, Miami Lakes, FL (US)

( * ) Notice: Subject to any disclaimer, the term of this patent is extended or adjusted under 35 U.S.C. 154(b) by 368 days.

(21) Appl. No.: 10/056,681

(22) Filed: Jan. 24, 2002

(65) Prior Publication Data

US 2003/0139797 A1 Jul. 24, 2003

(51) Int. Cl.[7] .................................. A61F 2/06
(52) U.S. Cl. ........................................ 623/1.13
(58) Field of Search ........................ 623/1.13, 1.15, 623/1.17, 1.23, 1.36; 606/191, 194

(56) References Cited

U.S. PATENT DOCUMENTS

| | | | |
|---|---|---|---|
| 5,122,154 A | * | 6/1992 | Rhodes ................... 623/1.13 |
| 5,667,523 A | * | 9/1997 | Bynon et al. ............ 623/1.13 |
| 5,865,723 A | | 2/1999 | Love |
| 5,922,020 A | * | 7/1999 | Klein et al. ............. 623/1.15 |
| 5,998,024 A | | 12/1999 | Frey et al. |
| 6,042,605 A | * | 3/2000 | Martin et al. ........... 623/1.13 |
| 6,187,034 B1 | * | 2/2001 | Frantzen ................. 623/1.11 |
| 6,558,414 B2 | * | 5/2003 | Layne .................... 623/1.13 |
| 6,602,282 B1 | * | 8/2003 | Yan ....................... 623/1.15 |
| 2001/0020181 A1 | | 9/2001 | Layne |
| 2003/0114918 A1 | * | 6/2003 | Garrison et al. ........ 623/1.13 |

* cited by examiner

Primary Examiner—Anhtuan T. Nguyen
Assistant Examiner—Jessica R. Baxter

(57) ABSTRACT

A covered stent comprising individual stent rings alternately loaded inside and outside of the covering material, wherein the rings are not connected to adjacent rings along the longitudinal axis.

18 Claims, 1 Drawing Sheet

COVERED SEGMENTED STENT

FIELD OF THE INVENTION

The present invention generally relates to medical devices, particularly stents and covered stents. More particularly, the present invention is directed to a covered stent comprising individual stent rings loaded inside and outside of the covering material.

BACKGROUND OF THE INVENTION

As background to a discussion of stents, one notes that in the 1970s, the technique of percutaneous transluminal coronary angioplasty (PTCA) was developed for the treatment of atherosclerosis. Atherosclerosis is the build-up of fatty deposits or plaque on the inner walls of a patients arteries; these lesions decrease the effective size of the artery lumen and limit blood flow through the artery, prospectively causing a myocardial infarction or heart attack if the lesions occur in coronary arteries that supply oxygenated blood to the heart muscles. The term stenosis refers to a narrowing or restriction in the diameter of a tubular structure, such as an artery. As a separate point, the application of balloon angioplasty to certain blood vessels has been limited by the risk of forming emboli during the procedure. For example, when angioplasty is applied to lesions in the carotid artery, there is the possibility of dislodging plaque from the lesion, which can enter the various arterial vessels of the brain and cause permanent brain damage.

In the angioplasty procedure, a guide wire is inserted into the femoral artery and is passed through the aorta into the diseased coronary artery. A catheter having a balloon attached to its distal end is advanced along the guide wire to a point where the sclerotic lesions limit blood flow through the coronary artery. The balloon is then inflated, compressing the lesions radially outward against the wall of the artery and substantially increasing the size of its internal lumen, to improve blood circulation through the artery.

A stent is a generally longitudinal tubular device formed of biocompatible material, and is useful in the treatment of stenoses, strictures or aneurysms in body vessels such as blood vessels. These devices are implanted within the vessel to reinforce collapsing, partially occluded, weakened or abnormally dilated sections of the vessel. Stents are typically employed after angioplasty of a blood vessel to prevent restenosis of the diseased vessel. While stents are most notably used in blood vessels, stents may also be implanted in other body vessels such as the urogenital tract and the bile duct. Stents generally include an open flexible configuration. This configuration allows the stent to be inserted through curved vessels. Furthermore, the stent configuration allows the stent to be configured in a radially compressed state for intraluminal catheter implantation.

In the present time, it is the case that stents are increasingly being used in place of or in addition to PTCA for treatment of atherosclerosis, with the intent of minimizing the need to repeatedly open an atherosclerotic artery. In fact, the passage through the atherosclerotic artery is so small, that the area of a stenosis often needs to be predilated with a small and low profile balloon in order to be able to position the stent delivery device and to deliver a self-expandable stent at the desired location of the stenosis. The need to predilate the artery necessitates the passage of a low profile balloon through the area of stenosis, dilatation of the artery, and removal of the predilatation balloon, followed by passage of the stent deployment device through the same area of steriosis. This manipulation of the balloon and then the stent within the narrowed artery, which contains irregular and friable plaque, can cause thromboembolic complications. (Friable plaque has the gross pathological appearance of degenerated, loose, fibroatheromatous debris. For example, dislodgment of a fragment of plaque can cause a stroke if it is not caught before it passes into the brain.)

Hence, it is desirable to provide a device that requires minimal manipulation within the area of a stenosis. It is further desired to provide a device that is capable of preventing any fragments of plaque that may become dislodged from passing up through the artery and into the brain. For friable or thrombotic stenoses, the covered stent of the present invention offers the benefit of holding the thrombus or friable material up against the vessel wall, and preventing prolapse through the open space between stent struts and potential embolism downstream. (A thrombus can be viewed as a clot—red blood cells held together by fibrin—that adheres to the wall of a blood vessel.) Thrombosis has been described as coagulation occurring in the wrong place or at the wrong time. The end result of thrombosis is an obstruction of the blood flow.

Several things can happen after a thrombus forms. The fibrinolytic system may completely degrade the clot allowing blood flow to return to normal. The thrombus may "propagate"—accumulate more fibrin and platelets and grow along the course of the vessel. The thrombus may become fibrotic and be incorporated into the wall of the blood vessel. In some cases new blood vessels may grow into the fibrotic thrombus and establish partial but reduced blood flow (recanalization). Thrombi may dislodge and travel to other sites in the circulation (thromboembolus). The major clinical consequences of thrombus formation are narrowing and occlusion of blood vessels, or the generation of an embolus. Both of these can lead to tissue ischemia or infarct.

Although a number of different designs for stents have been published, stents are generally configured as elongate cylindrical structures that are provided in a first state and can assume a second, different state, with the second state having a substantially greater diameter than the first state. A stent is implanted in a patient using an appropriate delivery system for the type of stent being implaced within the patient's arterial system. There are two basic types of stents—those that are expanded radially outward due to the force from an inflated angioplasty type balloon, such as the, Palmaz-Schatz® stent, and those that are self expanding, the SMART® nitinol stent (made of a nickel titanium alloy)

Stents may be used in combination with a PTCA procedure. Specifically, stents are sometimes used following a PTCA procedure if the artery is totally occluded or if the lesions have occluded a previously placed surgical graft. Typically, a stent constrained within an introducer sheath is advanced to a site within the patient's artery through a guide catheter. For the balloon-expanded type, after the introducer sheath is retracted, a balloon disposed inside the stent is inflated to a pressure ranging from about six to fourteen atmospheres. The force produced by the inflated balloon expands the stent radially outward beyond its elastic limit, stretching the vessel and compressing the lesion to the inner wall of the vessel. A self-expanding stent expands due to spring force following its implacement in the artery, after a restraining sheath is retracted from the compressed stent, or in the case of the nitinol version, the stent assumes its expanded memory state after being warmed above the martensitic transition temperature for the nitinol alloy (e.g., above 30° C.)

Following the expansion process, when the balloon catheter is used, the balloon is removed from inside the stent and the catheter and other delivery apparatus is withdrawn. The lumen through the vessel is then substantially increased, improving blood flow. After a stent or other endoluminal device is implanted, a clinical examination and either an angiography or an ultrasonic morphological procedure is performed to evaluate the success of the stent emplacement procedure in opening the diseased artery or vessel. These tests are typically repeated periodically, e.g., at six-month intervals, since restenosis of the artery may sometimes occur.

Implantable devices may be used in other contexts, such as for abdominal aortic aneurysms. The abdominal aortic aneurysm usually arises in the infrarenal portion of the diseased aorta, for example, below the kidneys. When left untreated, the aneurysm may eventually cause rupture of the sac with ensuing fatal hemorrhaging in a very short time. High mortality associated with the rupture led initially to transabdominal surgical repair of abdominal aortic aneurysms. Surgery involving the abdominal wall, however, is a major undertaking with associated high risks. There is considerable mortality and morbidity associated with this magnitude of surgical intervention, which in essence involves replacing the diseased and aneurysmal segment of blood vessel with a prosthetic device, typically is a synthetic tube, or graft, usually fabricated of polyester, Urethane, DACRON, TEFLON, or other suitable material, such as those disclosed in U.S. Pat. No. 5,998,024 (issued Dec. 7, 1999).

Generally, stents, grafts, and graft stents are implantable medical devices (sometimes termed implantable tubular prostheses) placed within blood vessels and other body passageways to treat disease conditions such as stenoses, occlusions, and aneurysms. Transluminal implantation of such devices requires that they be introduced to the site collapsed about or within an introduction device and released to self expand or are expanded by other mechanisms to an expanded tubular state providing a lumen of approximately the same size as the patent vessel or duct lumen.

Stents can be viewed as scaffoldings, of generally cylindrical symmetry, that function to physically support, and, if desired, expand the wall of the passageway. Typically, a stent consists of two or more struts or wire support members connected together into a lattice-like or open weave frame. Most stents are compressible for insertion through small cavities, and are delivered to the desired implantation site percutaneously via a catheter or similar transluminal device. Once at the treatment site, the compressed stent is expanded to fit within or expand the lumen of the passageway. Stents are typically either self-expanding or are expanded by inflating a balloon that is positioned inside the compressed stent at the end of the catheter. Intravascular stents are often deployed after coronary angioplasty procedures to reduce complications, such as the collapse of arterial lining, associated with the procedure.

Stents have a lattice-like structure, leaving spaces defined by the struts that form the stent. Such spaces can allow plaque from the lesion to fall through the stent and enter the blood stream during stent deployment. The spaces can also permit malignant tissue growth through the stent openings into the body passageway and can allow undesired contact between blood flowing through the blood vessel and damaged portions of the vessel. Covered stents, in which a polymeric material surrounds and is attached to the stent, have been proposed to alleviate the concerns associated with stent openings.

Diseased vessels are also treated with grafts. Grafts are generally tubular in morphology and are used to replace or create an anatomical passageway to provide a new conduit for fluid, e.g. blood. Grafts are often made from a portion of a vein, but can also be constructed from a synthetic material to form a synthetic graft. Like stents, synthetic grafts often are positioned percutaneously via a catheter, for instance, to be placed at the site of an aneurysm to prevent further dilation and possible rupture of the diseased vessel.

In certain instances, the graft material alone does not provide enough structural support for the graft, causing the graft to collapse and occlude or impede the flow of blood through the vessel. Grafts may be used with stents. Specifically, a graft may comprise a tube-shaped member having an inside diameter only slightly larger than the circumference of the deployed stent. The graft may be made of latex, silicone, polytetraflouroethylene, polyethylene, Dacron polyesters, polyurethane or other suitable biocompatible material. The graft material must be flexible and durable, so that it can withstand the effects of installation and usage. Depending on the material chosen, it may be preferable to form the graft in one of several ways. For example, the graft may be extruded, woven or formed by dipping a substrate in the desired material, removing the material from the substrate, and trimming the end of the material, so as to form a cylindrical tube having an opening at each end.

The graft is deployed simultaneously with the deployment of the stent. Prior to deployment, the graft is collapsed, with the collapsed stent inside or outside of it. As described, the stent and graft may then be inserted into a catheter, deployed, and expanded by pressurization of a balloon. A graft deployed and supported in this manner may be used to seal an aneurysm or similar defect in a vessel. The tissue of the vessel adjacent to the graft will grow onto the graft, so that the graft becomes an integral, reinforcing that part of the vessel wall and helping to reduce the risk of future ruptures at that location. For those cases wherein the material is synthetic, the combined structure is sometimes referred to as a synthetic stent graft. Stents are also placed at the ends of synthetic grafts to help secure the ends of the synthetic graft to vessel walls.

As a point of nomenclature, the term "stent" is sometimes used interchangeably in the prior art with "graft." In the present invention, the graft and the stent are separate elements. Of grafts, one has species of vascular grafts and artificial grafts. Vascular grafts classically are longer and have more continuous sidewalls than the purely metal stent. The expression "vascular graft" originally was used to described harvested blood vessels used to bypass a length of diseased or enlarged blood vessel, and the expression "artificial graft" typically connotes an elongated, biocompatible, tubular body mimicking the flexibility of the natural blood vessel it is intended to replace. In an open chest surgical procedure, the active attachment of such flexible vascular or artificial grafts to patent blood vessel ends is effected by suturing in a procedure referred to as anastomosis.

A challenge to the use of covered stents and synthetic stent grafts is keeping the stent covering attached to the stent. During expansion of the prosthesis, the covering and the stent have different expansion versus length properties, causing the cover to possibly detach from the stent, or bunch, creating an irregular blood flowpath which can adversely affect graft patency. Currently, covers are attached to stents by stitching or gluing, or by wholly embedding the stent into the polymeric cover material. When stitches are used, the cover is typically punctured at the stitch site, leaving an opening and a weak place in the cover that may tear or rip when the covered stent is expanded. Further, the act of suturing through the fabric creates potential leak paths for the blood. The present invention avoids attachment that breaches the graft material.

Separately in the prior art, using glue instead of stitches addresses the puncture problems, however, glue can be difficult to keep in place on the stent when attaching the cover material. Furthermore, in some cases, the glue itself does not provide a strong enough hold to keep the cover attached. When the stent is wholly embedded into the cover material, the covering is on both the inside and outside of the stent and may cause the profile of the covered stent to be larger than desired.

Another concern with wholly embedded stents is that crimping of the stent into a small profile for delivery becomes more difficult, as the cover material cannot fold independently from the stent, and becomes pinched in between the collapsing stent strut architecture. This prevents minimization of the crimped profile. Specifically, the present invention pertains to a manner of attaching the graft to the stent.

The present invention overcomes any difficulties associated with the current art related to the joining of the graft to the stent and to movement of the graft from the stent.

SUMMARY OF THE INVENTION

The present invention is generally directed to a stent design in which there is a covered stent comprising individual stent rings alternately loaded inside and outside of the covering material.

The present invention specifically has the advantages of holding the covering in place without double radial layers of metal or adhesives; holding cover material up from draping into the lumen; minimizing stent lengthening during crimping, because each ring acts independently (stent lengthening presents concerns during crimping of the covered stent.); maximizing stent flexibility (because there are no bridges, the covering determines the flexing force between segments).

The present invention comprises embodiments in which the covering is ePTFE or PET (DACRON); in which stent spacing is varied to optimize flexure properties; in which oversizing of internal stents is varied to the covering in order to maximize the fixation force at the ends; in which some of the uncovered stent is left to stick out of the end of covering to aid in anchoring the vessel; in which the internodal distance is varied (for embodiments employing ePTFE as a covering); in which the stent strength of internal versus external stents is varied, most particularly the embodiment with stronger internal stents.

DETAILED DESCRIPTION OF THE INVENTION

Figure 1:
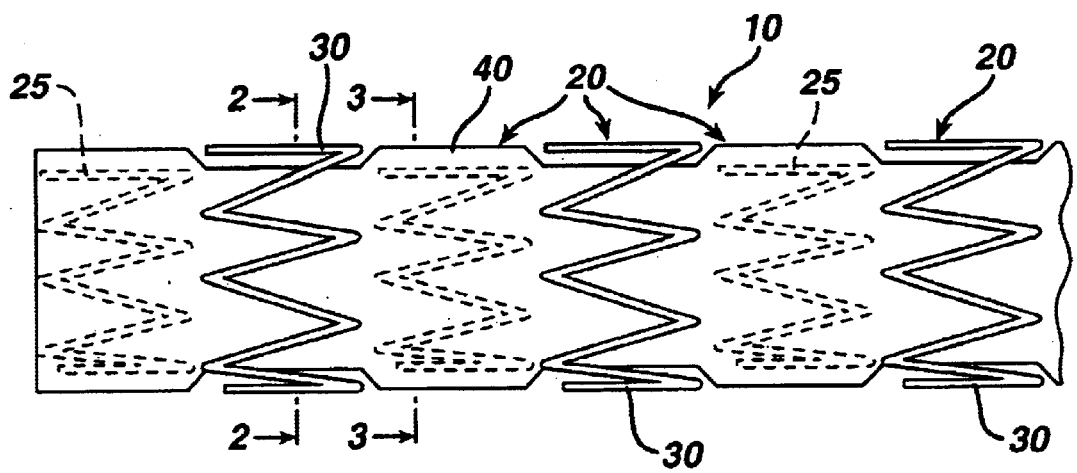
FIG. 1 Is a side plan view of the stent graft of the present invention.
Figure 2:
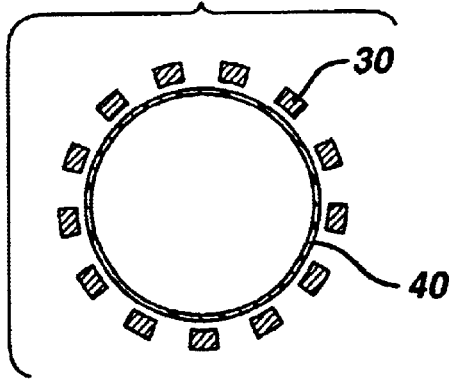
FIG. 2 is a cross sectional view of the stent graft of the present invention taken along lines 2–2 of FIG. 1.
Figure 3:
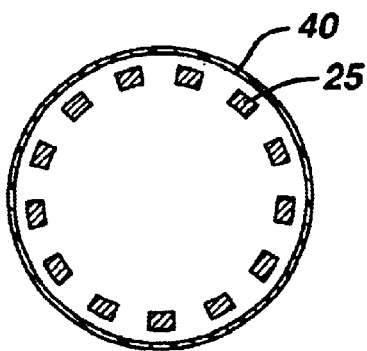
FIG. 3 is a cross sectional view of the stent graft of the present invention taken along lines 3–3 of FIG. 1.

The present invention is directed to a covered stent graft 10 comprised of individual stent rings 20 alternately loaded inside 25 and outside 30 of a covering material 40. The rings 20 supply radial strength. individually, but the rings are not connected to adjacent rings longitudinally.

The present invention is in the general art of stent grafts. Stent grafts are useful in treating two conditions—aneurysmal disease and thrombotic or friable stenotic lesions. For aneurysmal disease, the stent graft 10 is covered with a material 40 (typically DACRON or expanded polytetrafluoroethylene ("ePTFE") which allows the stent to span the aneurysmal vessel segment and to seal blood flow and pressure from reaching the aneurysmal sac. The fabric covering 40 typically is porous, but with small enough pores to coagulate acutely and to exclude the aneurysm from the transmitted blood pressure. Once the aneurysm is excluded, the sac is expected to shrink in size, and the risk of rupture is eliminated.

In the aneurysmal application, the main part of the stent graft 10 is "floating" in free space with only proximal and distal ends sealing rings 25, 30 against the healthy vessel segments adjacent to the aneurysm.

For friable or thrombotic stenoses, a covered stent graft 10 may offer the benefit of holding the thrombus or friable material up against the vessel wall, and preventing prolapses through the open space between stent struts, and potential embolism downstream.

Separately, there are problems in the repair of many abdominal aortic aneurysms. One such problem is that the aneurysm neck is often too short to permit adequate fixation with an expandable stent. (Generally, a length of two centimeters or more is needed for adequate anchoring of the graft.) Additionally, the aneurysm neck is frequently too heavily calcified to permit fixation with hooks, i.e., the hooks cannot penetrate areas of the aortic wall that have thick, calcified plaques. In other cases, the inner wall of the neck is thickened by soft, friable plaque or thrombus that makes fixation with hooks impossible or inadequate.

In the application for friable or thrombotic stenoses, the stent graft 10 opposes the vessel wall with rings 25, 30 along its entire length. This alignment is distinct from that found in the aneursymal application.

In terms of background, a graft is a typically a fabric or a covering. A stent is a structural element that supports the graft. Historically, grafts have been surgically implanted as substitutes for native vessels. The technology of stent grafts began with surgical grafts being supported endoluminally with early vascular stents. A problem solved by the present invention, is the poor connection between graft and stent found in prior art embodiments of stent grafts. An objective is to have stent grafts to evolve to become a composite of the two elements.

Many of the prior art devices have stent segments attached to the graft material with sutures. The need to make flexible structures has led the art to the use of segmented rigid stents, which articulate at the unsupported graft areas. In order to keep the segmented stents in place, such stents employ attachment to the graft fabric. The act of suturing through the fabric creates potential leak paths for the blood. The present invention avoids attachment that breaches the graft material.

Separately, an alternate method of fixing the graft to the stent is to sandwich a layer of graft between two stents. This sandwiching creates a large crimped profile. The present invention avoids both suturing and multiple stent layers at the same longitudinal location.

Generally, the present invention offers the following advantages:

1. No through graft perforations for fixation of material to the stent.—Perforations of the covering material are undesirable when trying to seal aneurysms. The present invention uses friction from alternating inside and outside segments to join the covering and the stent.

2. No double walls of material, as in stent "sandwiches", so that the profile is minimized.—The present invention allows graft material to move with respect to stents during crimping, which prevents pinching of the graft by the stent during crimping. In the prior art, longitudinally connected stents change length during crimping, but the graft does not change its length. The present invention reduces foreshortening of the stent overall versus a fully longitudinally connected stent.

The present invention minimizes, or eliminates, the need for staples or sutures for the attachment of the graft material to the stent. The act of suturing through the covering fabric is undesirable because it creates leak paths for the blood. The use of coating decreases flexibility.

In the prior art, stents are placed inside of graft tubes, and held in place by the force of the stent against the vessel wall. A desired structural graft is a composite material with the properties of both a graft and a stent.

It is an object of the present invention to assemble a woven DACRON (also denoted PET OR PETE), or TEFLON or other biocompatible graft material to a stent, while allowing for folding and compressibility of the graft semi-independently of the stent, yet still held in a multitude of locations to provide for good stent to graft apposition (movement together). Sometimes the following materials will be used: ePTFE, PET, UHMWPE (ultra high molecular weight polyethylene), polyester polyarylate, and PEEK (polyester ether ketone). Some prior art devices depend on manual sewing to define these stent to graft attachment points. The present invention allows for an advancement to eliminate the costly manufacturing technique of the prior art.

The covering of the present invention may be woven polyester made with mono or multi-filament yarn. The covering may comprise TEFLON. The covering may comprise DACRON.

The invention resolves other-problems in the prior art. Thin walled plastic stent grafts of the prior art can change diameter by wrinkling or folding. When the stent graft is fully open, the perimeter fabric is taut. When it is loaded into a catheter, the perimeter fabric folds in on itself (like a pleated skirt). A nitinol stent, or even a malleable steel stent, changes diameter through strut bending. Although the graft fibers also bend, they will bend out of plane, towards and away from the centerline of the graft. The stent struts bend within the circumference as the device diameter changes.

What is claimed is:

1. A covered stent comprising individual stent rings alternately loaded inside and outside a covering material, wherein the rings are not connected longitudinally; and wherein the stent rings loaded inside the covering material are stronger than the sent rings loaded outside the covering material.

2. The stent of claim 1 wherein the covering material is selected from the group consisting of ePTFE and PET.

3. The stent of claim 1 wherein some of the stent is uncovered to aid in anchoring the vessel.

4. The stent of claim 1 wherein foreshortening is reduced in comparison to a longitudinally connected stent.

5. The stent of claim 1 wherein there are no perforations through the covering material.

6. The stent of claim 1 where gaps between alternating stent rings when expanded are of sufficient length to prevent touching of the stent structures when they are crimped to the diameter at which they are delivered.

7. The stent of claim 1 where the features of the adjacent stent rings are aligned so that they do not interfere with one another when the composite stent is placed in a bend.

8. The stent of claim 1 wherein the covering material is selected from the group consisting of ePTFE, PET, UHMWPE (ultra high molecular weight polyethylene), polyester polyarylate, and PEEK (polyester ether ketone).

9. The stent of claim 1 wherein the stent rings loaded inside the covering are larger in their unconstrained state than the stents loaded on the outside of the covering.

10. A covered stent comprising individual stent rings alternately loaded inside and outside a covering material, wherein the rings are not connected longitudinally; and wherein the stein rings loaded inside the covering are larger in their unconstrained state than the stents loaded on the outside of the covering.

11. The stent of claim 10 wherein the covering material is selected from the group consisting of ePTFE and PET.

12. The stent of claim 10 wherein the stent rings loaded inside the covering material are stronger than the stent rings loaded outside the covering material.

13. The stent of claim 10 wherein some of the stent is uncovered to aid in anchoring the vessel.

14. The stent of claim 10 wherein foreshortening is reduced in comparison to a longitudinally connected stent.

15. The stent of claim 10 wherein there are no perforations through the covering material.

16. The stent of claim 10 where gaps between alternating stent rings when expanded are of sufficient length to prevent touching of the stent structures when they are crimped to the diameter at which they are delivered.

17. The stent of claim 10 where the features of the adjacent stent rings are aligned so that they do not interfere with one another when the composite stent is placed in a bend.

18. The stent of claim 10 wherein the covering material is selected from the group consisting of ePTFE, PET, UHMWPE (ultra high molecular weight polyethylene), polyester polyarylate, and PEEK (polyester ether ketone).

* * * * *